US008718951B2

(12) United States Patent
Mishra et al.

(10) Patent No.: US 8,718,951 B2
(45) Date of Patent: May 6, 2014

(54) METHODS, COMPUTER-ACCESSIBLE MEDIUM, AND SYSTEMS FOR GENERATING A GENOME WIDE HAPLOTYPE SEQUENCE

(75) Inventors: Bhubaneswar Mishra, New York, NY (US); Thomas Anantharaman, San Diego, CA (US); Sang Lim, Millburn, NJ (US); Pierre Franquin, Westborough, MA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/422,703

(22) Filed: Mar. 16, 2012

(65) Prior Publication Data

US 2013/0045879 A1    Feb. 21, 2013

Related U.S. Application Data

(63) Continuation-in-part of application No. 12/046,988, filed on Mar. 12, 2008, now Pat. No. 8,140,269.

(60) Provisional application No. 60/894,376, filed on Mar. 12, 2007.

(51) Int. Cl.
*G01N 33/48*    (2006.01)
*G06F 19/20*    (2011.01)

(52) U.S. Cl.
CPC ..................... *G06F 19/20* (2013.01)
USPC .......................................................... 702/20

(58) Field of Classification Search
CPC ......... G06F 19/12; G06F 19/16; G06F 19/18; G06F 19/20; G06F 19/22; G06F 19/24; G06F 19/26; G06F 19/28; G06F 19/706
USPC .......................................................... 702/20
See application file for complete search history.

(56) References Cited

PUBLICATIONS

Moser et al. "Sequence-Specific Cleavage of Double Helical DNA by Triplex Helix Formation" Science (1987) vol. 238, pp. 645-650.*
Lai et al., "A Shotgun Optical Map of the Entire *Plasmodium falciparum* Genome", Nature Genetics, Nov. 1999, vol. 23*.
Casey et al., "Placing Probes Along the Genome using Pair-wise Distance Data", Probe Distance, Aug. 2000*.
Lim et al., "Shotgun Optical Maps of the Whole *Escherichia coli* 0157:H7 Genome", Genome Research, 2001, vol. 11*.
Jing et al., "Automated High Resolution Optical Mapping using Arrayed, Fluid-fixed DNA Molecules", Proc. natl. Acad. Sci. USA, Jul. 1998, vol. 95*.
International Search Report and Written Opinion for PCT/US2008/56648 dated Sep. 23, 2008.

\* cited by examiner

*Primary Examiner* — Jerry Lin
(74) *Attorney, Agent, or Firm* — Andrews Kurth LLP

(57) ABSTRACT

Methods, computer-accessible medium, and systems for generating a genome wide probe map and/or a genome wide haplotype sequence are provided. In particular, a genome wide probe map can be generated by obtaining a plurality of detectable oligonucleotide probes hybridized to at least one double stranded nucleic acid molecule cleaved with at least one restriction enzyme, and detecting the location of the detectable oligonucleotide probes. For example, genome wide haplotype sequence can be generated by analyzing at least one genome wide restriction map in conjunction with at least one genome wide probe map to determine distances between restriction sites of the genome wide restriction map(s) and locations of detectable oligonucleotide probes of the genome wide probe map(s) and defining a consensus map indicating restriction sites based on the genome wide restriction map(s) and/or locations of detectable oligonucleotide probes based on each of the genome wide probe map(s).

27 Claims, 2 Drawing Sheets

METHODS, COMPUTER-ACCESSIBLE MEDIUM, AND SYSTEMS FOR GENERATING A GENOME WIDE HAPLOTYPE SEQUENCE

CROSS-REFERENCE TO RELATED APPLICATION(S)

This application is a continuation-in-part application of U.S. patent application Ser. No. 12/046,988, filed on Mar. 12, 2008, that issued as U.S. Pat. No. 8,140,269 on Mar. 20, 2012, which claims priority from U.S. Provisional Patent Application No. 60/894,376, filed on Mar. 12, 2007, both of which are hereby incorporated by reference in their entireties.

STATEMENT REGARDING FEDERALLY SPONSORED RESEARCH

The present disclosure was developed, at least in part, using Government support under Contract No. 1 R21 HG003714-01 awarded by the NHGRI of National Institutes of Health. Therefore, the Federal Government may have certain rights in the present disclosure.

FIELD OF THE PRESENT DISCLOSURE

The present disclosure relates generally to methods, computer-accessible medium, and systems for generating genome wide probe maps. The present disclosure also relates generally to use of genome wide probe maps, e.g., in methods, computer-accessible medium, and systems for generating genome wide haplotype sequences, which may be read at a pre-defined level of accuracy.

BACKGROUND INFORMATION

Recent advances in genomic sciences, high throughput technologies, and infusion of domain-experts from various quantitative subjects have created new opportunities for identifying many of the genes commonly implicated in diseases, and elucidating many of the cellular pathways upon which they act. Advances in the genomic sciences include component technologies generally explored within various mapping approaches such as, e.g., optical mapping and array-mapping techniques. Such techniques are described, e.g., in Z. Lai. et al., "A Shotgun Sequence-Ready Optical Map of the Whole *Plasmodium falciparum* Genome," Nature Genetics, 23(3): 309-313, 1999; A Lim et al., "Shotgun optical maps of the whole *Escherichia coli* O157:H7 genome," Genome Research, 11(9): 1584-93, September 2001; W. Casey, B. Mishra and M. Wigler, "Placing Probes along the Genome using Pair-wise Distance Data," Algorithms in Bioinformatics, First International Workshop, WABI 2001 Proceedings, LNCS 2149:52-68, Springer-Verlag, 2001; B. Mishra, "Comparing Genomes," Special issue on "Biocomputation:" Computing in Science and Engineering, pp 42-49, January/February 2002; J. West, J. Healy, M. Wigler, W. Casey, and B. Mishra, "Validation of *S. pombe* Sequence Assembly by Micro-array Hybridization," Journal of Computational Biology, 13(1): 1-20, January 2006.

For example, after a decade-long effort directed at optical mapping, single molecule optical mapping technology was developed for clones in 1998 (see, e.g., J. Jing et al., "Automated High Resolution Optical Mapping Using Arrayed, Fluid Fixated, DNA Molecules," Proc. Natl. Acad. Sci. USA, 95:8046-8051, 1998) and for whole microbial genomes in 1999 (see, e.g., J. Lin et al. "Whole-Genome Shotgun Optical Mapping of *Deinococcus radiodurans*," Science, 285:1558-1562, September 1999). In particular, a genome wide restriction map of a single nucleic acid molecule, e.g., double stranded DNA, may be generated using optical mapping techniques, e.g., fluorescent microscopy (see, e.g., J. Jing et al., "Automated High Resolution Optical Mapping Using Arrayed, Fluid Fixated, DNA Molecules," Proc. Natl. Acad. Sci. USA, 95:8046-8051, 1998).

An ordinarily skilled artisan would know how to generate a genome wide restriction map. Briefly, uncloned DNA (e.g., DNA directly extracted from cells after lysis) may be randomly sheared into approximately 0.1-2 Mb pieces and attached to a charged glass substrate, where the DNA may be cleaved with a restriction enzyme, then stained with a dye (e.g., a fluorescent dye). The restriction enzyme cleavage sites appear as breakages in the DNA under e.g., a fluorescent microscope. Using predefined techniques, the optical mapping of breakages produces a genome wide restriction map.

Although optical mapping methods have been used to generate genome wide restriction maps of whole prokaryotic and eukaryotic genomes, such methods have not been used for generating genome wide haplotype sequences.

Accordingly, at least one of the objects of the present disclosure present disclosure is to address such deficiencies and issues.

SUMMARY OF EXEMPLARY EMBODIMENTS

It has been determined, according to an exemplary embodiment of the present disclosure, that optical mapping may also be used to produce genome wide probe maps, which, when analyzed in conjunction with at least one genome wide restriction map, may be used to generate a genome wide haplotype sequence. Accordingly, provided herein are novel methods, computer-accessible medium, and systems for generating either or both genome wide probe maps and genome wide haplotype sequences using optical mapping techniques. These exemplary methods, computer-accessible medium, and systems may provide powerful strategies that may be capable of statistically combining disparate genomic information, and novel chemical protocols that may, in parallel, manipulate and interrogate a large number of single DNA molecules in various environments.

Exemplary embodiments of methods, computer-accessible medium, and systems for generating genome wide probe maps are described, where at least one detectable oligonucleotide probe can include at least one solid nucleotide (e.g., adenine "A", thymine "T", cytosine "C", guanine "G") and at least one gap nucleotide (e.g., a universal base), wherein a pattern of solid and gap nucleotides can be known. Further, the detectable oligonucleotide probe(s) can be selected according to a quality metric that is based at least in part on the selected pattern of solid and gap nucleotides. The exemplary quality metric can have a minimum or maximum threshold, such as, e.g., 0.1, 0.2, or 0.3.

Exemplary embodiments of methods, computer-accessible medium, and systems for generating genome wide probe maps are provided, e.g., for use in generating a genome wide haplotype sequence, i.e., the nucleotide sequence of a whole diploid genome at the haplotypic level. Also provided are exemplary embodiments of methods, computer-accessible medium, and systems for generating genome wide haplotype sequences. Various exemplary applications of such methods, computer-accessible medium, and systems can include analyzing patient genomes to predict susceptibility to various genetic or genomic diseases, or analyzing patient genomes to diagnose genomic instability and mutations as the basis of cancer. The exemplary embodiments of the present disclosure may also have agricultural and biomedical applications in drug-or-vaccine discovery, understanding behavior of a cell in an altered state (e.g., cancer, neuro-degeneration, or autoimmune disease, etc.) genetically modifying a natural wild-type organism, genetic engineering, etc. Other exemplary applications may include understanding neural behavior, evolutionary processes, and genome evolution and aging.

Exemplary embodiments of the present disclosure relate generally to methods, computer-accessible medium, and systems for generating a genome wide probe map. For example, described herein are methods for generating a genome wide probe map by possibly (a) obtaining a plurality of detectable oligonucleotide probes hybridized to at least one double stranded nucleic acid molecule cleaved with at least one restriction enzyme, and (b) detecting the location of the detectable oligonucleotide probes to generate the genome wide probe map.

Further described herein is an exemplary computer-accessible medium having stored thereon computer executable instructions for generating a genome wide probe map. When the executable instructions are executed by a processing arrangement, such instructions configure the processing arrangement to (a) obtain a plurality of detectable oligonucleotide probes hybridized to at least one double stranded nucleic acid molecule cleaved with at least one restriction enzyme, and (b) detect the location of the detectable oligonucleotide probes to generate the genome wide probe map.

Exemplary systems for generating a genome wide probe map are also provided. In one exemplary embodiment, such system can include a processing arrangement which, when executed, is configured to (a) obtain a plurality of detectable oligonucleotide probes hybridized to at least one double stranded nucleic acid molecule cleaved with at least one restriction enzyme, and (b) detect the location of the detectable oligonucleotide probes to generate the genome wide probe map.

The exemplary embodiments of the present disclosure also relates generally to use of genome wide probe maps, e.g., in methods, computer-accessible medium, and systems for generating a genome wide haplotype sequence. For example, it is possible to generate a genome wide haplotype sequence by (a) analyzing at least one genome wide restriction map in conjunction with at least one genome wide probe map to determine distances between restriction sites of the at least one genome wide restriction map and locations of detectable oligonucleotide probes of the at least one genome wide probe map, and (b) defining a consensus map indicating restriction sites based on each of the at least one genome wide restriction map and locations of detectable oligonucleotide probes based on each of the at least one genome wide probe map to generate the genome wide haplotype sequence.

Addition, an exemplary computer-accessible medium can be provided having stored thereon computer executable instructions for generating a genome wide haplotype sequence. When the executable instructions are executed by a processing arrangement, configure the processing arrangement to (a) analyze at least one genome wide restriction map in conjunction with at least one genome wide probe map to determine distances between restriction sites of the at least one genome wide restriction map and locations of detectable oligonucleotide probes of the at least one genome wide probe map, where the detectable oligonucleotide probe(s) can include at least one solid nucleotide and at least one gap nucleotide, wherein a pattern of solid and gap nucleotides is known, and (b) define a consensus map indicating restriction sites based on each of the at least one genome wide restriction map and locations of detectable oligonucleotide probes based on each of the at least one genome wide probe map to generate the genome wide haplotype sequence.

Exemplary systems for generating a genome wide haplotype sequence are also provided. In one exemplary embodiment, such system can include a processing arrangement which, when executed, (a) analyzes at least one genome wide restriction map in conjunction with at least one genome wide probe map to determine distances between restriction sites of the at least one genome wide restriction map and locations of detectable oligonucleotide probes of the at least one genome wide probe map, wherein the detectable oligonucleotide probe(s) can include at least one solid nucleotide and at least one gap nucleotide, wherein a pattern of solid and gap nucleotides is known, and (b) defines a consensus map indicating restriction sites based on each of the at least one genome wide restriction map and locations of detectable oligonucleotide probes based on each of the at least one genome wide probe map to generate the genome wide haplotype sequence.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which.

DETAILED DESCRIPTION OF EXEMPLARY EMBODIMENTS

Figure 1:
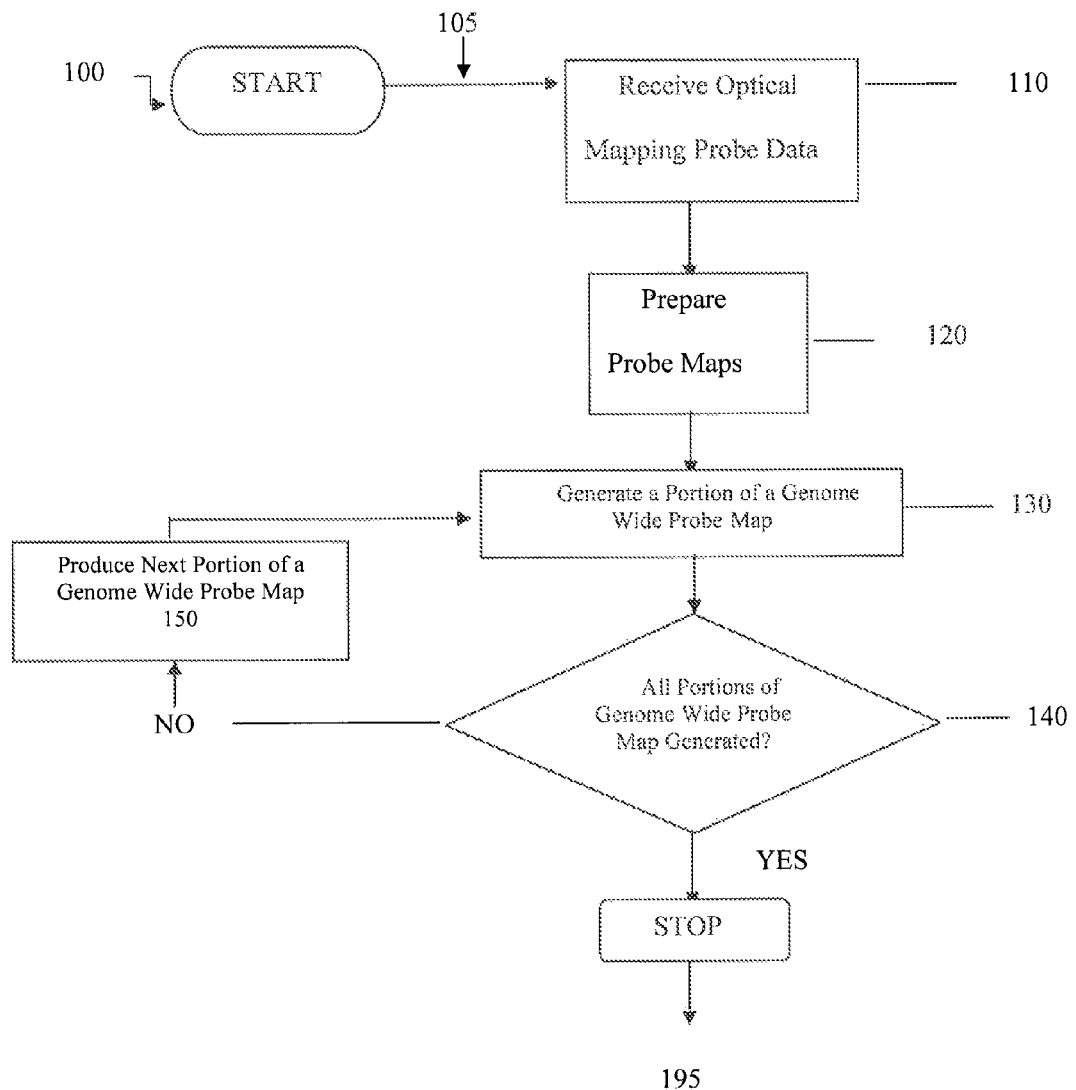
FIG. 1 is a flow diagram of a method for generating at least one genome wide probe map in accordance with the present disclosure.

As discussed herein; recent advances, particularly in the use of optical mapping to generate a genome wide restriction map, have created new opportunities for identifying many of the genes commonly implicated in disease and elucidating many of the cellular pathways upon which they act. In order to exploit these opportunities, the exemplary embodiments of the present disclosure can provide robust, efficient, and inexpensive technologies that may produce genome wide haplotype sequences, which may allow a study of genomic variations at multiple scales and across multiple species. As such, it has been determined that optical mapping may be used to generate genome wide probe maps, which when analyzed in conjunction with at least one genome wide restriction map, may be used to generate a genome wide haplotype sequence. Accordingly, described herein are exemplary embodiments of methods, computer-accessible medium, and systems, for generating a genome wide probe map. Further, also described herein are exemplary embodiments of methods, computer-accessible medium, and systems for generating a genome wide haplotype sequence.

Exemplary embodiments of the present disclosure, which can be directed to whole genome sequencing, e.g., generating a genome wide haplotype sequence, can employ certain features capable of integrating two techniques. The first exemplary technique is single molecule optical mapping described above, and e.g., in both Z. Lai. et al., "A Shotgun Sequence-Ready Optical Map of the Whole *Plasmodium falciparum* Genome," Nature Genetics, 23(3): 309-313, 1999; and in A Lim et al., "Shotgun optical maps of the whole *Escherichia coli* O157:H7 genome," Genome Research, 11(9): 1584-93, September 2001. Optical mapping may be used to prepare a restriction map associated with at least one chromosome and/or produce portions of a genome wide restriction map, which may be statistically combined to generate a genome wide restriction map of random and/or single double stranded nucleic acids, e.g., genomic DNA molecules, of sizable length, for example, of about 400 Kb. In other words, raw optical mapping data may be assembled by processing arrangements, e.g., computers, into genome wide restriction maps (see, e.g., PCT Application Publication No. WO 2004/046889). A second exemplary technique relates to technology involving oligonucleotide probe hybridization to a nucleic acid molecule, e.g., double stranded DNA.

A. Generating an Exemplary Genome Wide Probe Map

In one exemplary embodiment, a method for generating a genome wide probe can be provided, which can (a) obtain a plurality of detectable oligonucleotide probes hybridized to at least one double stranded nucleic acid molecule cleaved with at least one restriction enzyme, and (b) detect the location of the detectable oligonucleotide probes to generate the genome wide probe map.

i. Hybridization of a Plurality of Oligonucleotide Probes

An ordinarily skilled artisan would understand that (1) the protocol for hybridizing a plurality of detectable oligonucleotide probes to a double stranded nucleic acid molecule is dependent on the type of detectable oligonucleotide probes used, and (2) the lengths of detectable oligonucleotide probes used. An ordinarily skilled artisan would also recognize which well-known hybridization protocol to use with which type and length of oligonucleotide probe. Further, an ordinarily skilled artisan would recognize that an oligonucleotide probe may be detectable because it is labeled with, e.g., a fluorescent label, a radioactive label, etc., and that the labels may be detected by conventional means.

Certain exemplary embodiments of the present disclosure may include the utilization of detectable oligonucleotide probes that hybridize with double stranded nucleic acid molecules, e.g., genomic double stranded DNA (dsDNA) without breaking the nucleic acid molecule. As a result, the nucleic acid molecule may be deposited intact on a surface, similar to the technique of restriction enzyme optical mapping, with very little change to the protocol. Regular oligonucleotide probes (as used in FISH, for example), typically hybridize at about 75° C., which is above the melting temperature of 65° C. for dsDNA. This can generally result in the breaking of both strands of the dsDNA at irregular intervals, which may produce a random "necklace" of DNA balls typically seen in Fibre-FISH instead of a single continuous segment of DNA on the surface. Such breakage is described, e.g., in Jeffrey M. Levsky and Robert H. Singer, "Fluorescence in situ hybridization: past, present and future," Journal of Cell Science, 116 (14): 2833-2003; in H. de Jong, "Visualizing DNA domains and sequences by microscopy: a fifty-year history of molecular cytogenetics," Genome 46: 943-946 (2003); and in H. Weier, "DNA Fiber Mapping Techniques for the Assembly of High-resolution Physical Maps," The Journal of Histochemistry & Cytochemistry, 49(8): 939-948, 2001. In addition, regular oligonucleotide probes may likely only hybridize reliably and selectively if the oligonucleotide probes are 15 bp or longer. An ordinarily skilled artisan would understand that other conventional types of probes of varying lengths may be used, where such oligonucleotide probes may hybridize with dsDNA without breaking the dsDNA, and where the oligonucleotide probes may be used reliably and with high selectivity even at lengths of 6 bp. For example, varying lengths of L-mers include oligonucleotide probes where L equals 6 base pairs, 7 base pairs, 8 base pairs, 9 base pairs, 10 base pairs, 11 base pairs, 12 base pairs, 13 base pairs, 14 base pairs, 15 base pairs, 20 base pairs, etc. A list of some exemplary DNA probes is provided below:

Locked Nucleic Acid (LNA) oligonucleotide probes are single stranded probes similar to the more well known Peptide Nucleic Acid (PNA) oligonucleotide probes. LNA probes have greater specificity to single stranded DNA (ssDNA) than PNA and are described, e.g., in A. Simeonov et al., "Single Nucleotide Polymorphism Genotyping using Short, Fluorescently Labeled Locked Nucleic Acid (LNA) Probes and Fluorescence Polarization Detection," Nucleic Acids Research, 30(17): e91, 2002; and in V. Demidov, "PNA and LNA Throw Light on DNA," Trends in Biotechnology, 21(1), January 2003.

Since both LNA and PNA oligonucleotide probes may hybridize with double stranded DNA (dsDNA) below the dsDNA melting point (i.e., 65° C.), e.g., hybridization of LNA and/or PNA to dsDNA may occur, e.g., at 55° C., most of the breakage of the dsDNA may be avoided. Further, at 55° C., the dsDNA temporarily denatures into two complementary ssDNA at various local points and allows the LNA or PNA oligonucleotide probes to hybridize. Since the LNA-ssDNA (or PNA-ss-DNA) binding constant can be much higher than that of dsDNA, at complementary locations the LNA (or PNA) oligonucleotide probes remain hybridized, while at other locations the two ssDNA strands may anneal back into dsDNA.

LNA has an even stronger binding constant than PNA, and thus, it may be possible to reliably use 6 bp LNA oligonucleotide probes for hybridizing to nucleic acid molecules that are GC rich (e.g., 50% or more GC). A skilled artisan would understand that for LNA oligonucleotide probes of 7 bp may be used if only 2 GC bases are present and LNA oligonucleotide probes of 8 bp may be used if a single GC base is present. Such techniques are described, e.g., in A. Simenov et al., "Single Nucleotide Polymorphism Genotyping using Short, Fluorescently Labeled Locked Nucleic Acid (LNA) Probes and Fluorescence Polarization Detection," Nucleic Acids Research, 30(17): e91, 2002. Commercially available LNA probes may also be used for this purpose.

Triplex Forming Oligonucleotide (TFO) probes are single stranded probes that hybridize directly with dsDNA, i.e., without dsDNA first denaturing, by forming a triple-stranded DNA. Such TFO oligonucleotide probes were originally developed for the purpose of suppressing gene expression in vivo as described, e.g., in M. Koizumi et al., "Triplex Formation with 2'-),4'-C-Ethylene-Bridged Nucleic Acids (ENA) Having C3'-Endo Conformation at Physiological pH," Nucleic Acids Research, 31(12): 3267-3273, 2003, but they may also be used as oligonucleotide probes. A common TFO oligonucleotide probe may include LNA, PNA, and/or DNA, e.g., may be a 50% mix of LNA and DNA. Superior TFOs may also be formed from ethylene nucleic acid (ENA). The melting temperature of TFO oligonucleotide probes may range from 28° C.-41° C. for LNA-DNA mixes and 42° C.-57° C. for different types of ENA-DNA mixes as described, e.g., in M. Koizumi et al., "Triplex Formation with 2'-),4'-C-Ethylene-Bridged Nucleic Acids (ENA) Having C3'-Endo Conformation at Physiological pH," Nucleic Acids Research, 31(12): 3267-3273, 2003. TFO oligonucleotide probes may be more stable with a higher melting temperature. However, ENA probes may not yet be commercially available but may be custom-synthesized by methods well-known in the art.

Double stranded oligonucleotide probes may also be used. A nonlimiting example of a double stranded oligonucleotide probe is pseudo-complementary PNA (pcPNA), which is a form of a single stranded PNA oligonucleotide probe that does not hybridize with itself. Such probes are described, e.g., in V. Demidov, "PNA and LNA Throw Light on DNA," Trends in Biotechnology, 21(1), January 2003; and in 1. Smolina et al., "Sequence-Universal Recognition of Duplex DNA by Oligonucleotides via Pseudocomplementarity and Helix Invasion," Chemistry & Biology, 10: 591-595, July 2003. Complementary pairs of such pcPNA probes may be used to hybridize with both strands of the dsDNA. The two pcPNA-DNA hybrids formed may be more stable than dsDNA. This exemplary technique may provide a fast hybridization (e.g., under one hour) and excellent mismatch rejection. Similarly to ENA based TFO probes, pcPNA probes may not be commercially available but may be custom synthesized using well-known methods.

ii. Double Stranded Nucleic Acid Molecule Cleaved with a Restriction Enzyme

A double stranded nucleic acid molecule (e.g., dsDNA) cleaved with at least one restriction enzyme may be provided by known methods. For example, a genome wide restriction map can often be generated using such double stranded nucleic acid molecules cleaved with at least one restriction enzyme (see, e.g., PCT Application Publication No. WO 2004/046889). For example, a restriction enzyme may be used with an immobilized double stranded nucleic acid molecule such that the nucleic acid molecule is cleaved to result in average restriction fragment sizes of about 2-16 Kb and at least 100× coverage (50× per haplotype).

Accordingly, as described herein, certain exemplary embodiments of the present disclosure include a plurality of detectable oligonucleotide probes that are hybridized with at least one double stranded nucleic acid molecule, e.g., dsDNA, cleaved with at least one restriction enzyme without breaking the double stranded nucleic acid molecule. As a result, genomic DNA may still be deposited intact on a surface, similar to the technique of restriction enzyme optical mapping, with very little change to the protocol. In one exemplary embodiment, a double stranded nucleic acid molecule cleaved with at least one restriction enzyme can provide both the data to generate a restriction enzyme map and a scaffold for generating a genome wide probe map and/or a genome wide haplotype sequence.

As such, the exemplary method for generating a genome wide probe map may also be used to simultaneously generate a genome wide restriction map for the immobilized double stranded nucleic acid molecule. Restriction enzyme digests, even for dsDNA immobilized on a coverslip, may be typically about 90% effective, whereas oligonucleotide probe hybridization may often be only about 30% effective (e.g., only about 30% of the matching probe sites may be visible in an image). To assemble genome wide probe maps including optical mapping restriction data for a genome wide restriction map, a false negative rate that generally does not exceed a value of about 30% per marker site may be required as described, e.g., in T. Ananthararnan et al. "A Probabilistic Analysis of False Positives in Optical Map Alignment and Validation," WABI2001, August 2001. A likely false negative rate of about 70% for probe maps may be circumvented using the following exemplary technique:

(a) hybridizing a plurality of detectable oligonucleotide probes to at least one double stranded nucleic acid molecule (e.g., double stranded DNA);

(b) depositing the plurality of detectable oligonucleotide probes hybridized to the double stranded nucleic acid molecule on a surface, e.g., a coverslip;

(c) cleaving the surface-mounted double stranded nucleic acid molecule with at least one restriction enzyme, e.g., similar to the technique used with conventional optical mapping to generate a restriction map; and (d) staining the double stranded nucleic acid with a detectable dye, e.g., YOYO.

This exemplary process/technique may generate a genome wide probe map for any probe sequence using standard coverslips covered with double stranded nucleic acid molecules using a molecular-combing-like technique for flow deposition of the double stranded nucleic acid molecules. An ordinarily skilled artisan would also recognize that in the methods provided herein, the double stranded nucleic acid molecule may first be immobilized, e.g., deposited on a coverslip and cleaved with a restriction site, prior to hybridization with a plurality of selected oliognucleotide probes and/or prior to probe extension methods.

iii. Detecting Detectable Oligonucleotide Probes

The plurality of detectable probes hybridized to at least one double stranded nucleic acid may then be detected by well-known methods, e.g., microscopy. As a nonlimiting example, a coverslip comprising a plurality of detectable oligonucleotide probes hybridized to at least one double stranded nucleic acid molecule cleaved with at least one restriction enzyme may be imaged at least once to detect the location of the detectable probes and optionally again to detect the distances between restrictions sites. In one exemplary embodiment, a genome wide probe map indicates both the locations of the detectable oligonucleotide probes and the distances between restrictions sites.

An ordinarily skilled artisan would understand that the microscopy used to image the detectable oligonucleotide probes is dependent on the detectable label and staining dye used. For example, if a fluorescent label is used for the oligonucleotide probes and a fluorescent dye is used to stain the double stranded nucleic acid molecule, fluorescent microscopy should be used.

FIG. 1 shows a flow diagram of an exemplary embodiment of a method for generating at least one genome wide probe map. This exemplary method may be performed by a processing arrangement 100, for example, but not limited to, a computer that includes a microprocessor, and using instructions stored on a computer-accessible medium (RAM, ROM, hard drive, or other storage device). The processing arrangement 100 can receive data 110, which may be optical mapping probe data from a plurality of detectable oligonucleotide probes hybridized to at least one double stranded nucleic acid molecule cleaved with at least one restriction enzyme indicating the location of the detectable oligonucleotide probes. Then, in step 120, the processing arrangement 100 may prepare a probe map associated with at least one chromosome. In step 130, a portion of at least one genome wide probe map can be produced. In step 140, the processing arrangement can determine whether all portions of the at least one genome wide probe map have been produced. If not, in step 150, a next portion of the at least one genome wide probe map may be produced. If all portions of the at least one genome wide probe map have been produced, the exemplary method stops in step 160, whereby the processing arrangement can use a procedure to combine all the portions to generate a genome wide probe map.

Also shown in FIG. 1, the processing arrangement 100 may be provided with an input arrangement 105, which may include e.g., a wired network, a wireless network, the internet, an intranet, etc. In addition, the processing arrangement 100 may be provided with an output arrangement 195, which may include, e.g., a wired network, a wireless network, the interne, an intranet, etc.

Accordingly, a genome wide genome probe map may be generated by, e.g., enumerating ordered occurrences of a known oligonucleotide probe sequence along double stranded nucleic acid cleaved by a restriction enzyme, which can be obtained by hybridizing the double stranded nucleic acid molecule with detectable oligonucleotide probes, detecting the location of the oligonucleotide probes and assembling the data similarly to the Gentig/Haptig procedure applied to assemble genome wide restriction maps created by restriction enzyme cleavage. Such exemplary procedures are described in greater detail herein.

B. Generating a Genome Wide Haplotype Sequence

The data resulting from microscopy of a plurality of oligonucleotide probes hybridized to at least one double stranded nucleic acid molecule probes may be assembled by exemplary processing arrangements such as, e.g., computers, to generate genome wide probe maps of locations of the detectable oligonucleotide probes of known sequences, e.g., 6 bp LNA oligonucleotide probe sequences, and/or distances between restriction sites. An ordinarily skilled artisan can recognize that although the raw sizing may not be as accurate as optical mapping to generate a genome wide restriction map, by adding the same restriction sites to the nucleic acid molecules with the probe sites, the sizing may be renormalized every 2-16 Kb, and may be used to generate a genome wide haplotype sequence. Thus, certain exemplary embodiments of the present disclosure also relate to methods, computer-accessible medium, and systems for generating genome wide haplotype sequences.

Described herein are exemplary methods for generating a genome wide haplotype sequence which (a) analyze at least one genome wide restriction-map in conjunction with at least one genome wide probe map to determine distances between restriction sites of the at least one genome wide restriction map and locations of detectable oligonucleotide probes of the at least one genome wide probe map, and (b) define a consensus map indicating restriction sites based on each of the at least one genome wide restriction map and locations of detectable oligonucleotide probes based on each of the at least one genome wide probe map to generate a genome wide haplotype sequence.

i. Analyzing Genome Wide Restriction Maps with Genome Wide Probe Maps

Exemplary embodiments of the present disclosure can result in the analysis of at least one genome wide restriction map in conjunction with at least one genome wide probe map to align the restriction sites of each of the at least one genome wide restriction map with the restrictions sites of each of the at least one genome wide probe maps, e.g., to determine distances between restriction sites of the at least one genome wide restriction map and locations of detectable oligonucleotide probes of the at least one genome wide probe map.

At least one genome wide restriction map may be the result of a prior optical mapping protocol, e.g., whereby all restriction data has been pooled using conventional optical mapping to generate a genome wide restriction map. Further, such genome wide restriction map(s) may be provided as part of a database of genome wide restriction maps.

Even though only 30% of the detectable oligonucleotide probes may be located, e.g., imaged, as long as 70% or more distances between restriction sites are also determined, e.g., imaged, each double stranded nucleic acid molecule fragment of sufficient length (150 kb or longer) of a genome wide probe map generated as described herein may be analyzed and reliably aligned with a at least one genome wide restriction map.

For example, an exemplary probe map may be generated for all possible sequences for a probe of a certain length, e.g., an oligonucleotide probe of about 6 bp (i.e., 2080 possible sequences), which may occur about every 2 Kb in a genome (including their reverse complements). The restriction sites of e.g., all 2080 probe maps may be aligned with each other, as these sites can occur about every 2-16 Kb. In a certain exemplary embodiment, a few of the 6 bp LNA probes (e.g. reverse-palindromes) may be unworkable. However, this may not present an obstacle to performing the exemplary procedures described herein, as construction of a complete set of all possible 2080 probe maps may not be necessary.

ii. Exemplary Techniques to Generate Genome Wide Probe Maps and/or Haplotype Sequences Once the genomic DNA fragments have been reliably aligned relative to each other, a consensus map indicating restriction sites based on each of the at least one genome wide restriction map and locations of detectable oligonucleotide probes base done, each of the at least one genome wide probe map may be defined, provided sufficient coverage is available to overcome the 70% false negative rate for the oligonucleotide probes. In certain exemplary embodiments, restrictions sites based on each of the at least one genome wide restriction map and locations of detectable oligonucleotide probes based on each of the at least one genome wide probe map can be indicated on a consensus map to generate a genome wide haplotype sequence.

Errors introduced by the experimental and analytical processes (e.g., non-uniform staining, failure of restriction enzyme to cleave, random breakages in the nucleic acid molecule that are mistaken for a cleavage site. introduction of additional pseudo-cleavage sites by faulty imaging, failure of imaging to detect cleavage sites that produce very small gaps, the combination of two pieces into a single larger piece, etc.) may manifest as the following exemplary types of errors in raw maps:

(a) errors in the measurement of fragment sizes or distances between restriction sites (typically 10% for a 30 Kb fragment), (b) errors in determining restriction sites, e.g., missing restriction sites (typically 10-20% of restriction sites may be false negatives) and/or false restriction sites (typically 2-10% of restriction sites may be false positives), and (c) errors in detection, e.g., missing small fragments (typically half of all fragments under 1 Kb may be missing and most fragments under 0.4 Kb may be missing).

An exemplary map assembly software may be used to assemble probe maps to generate genome wide probe maps based on overlaps from different detectable oligonucleotide probes (e.g., from any of the overlapping 2080 oligonucleotide probe maps of a double stranded nucleic acid hybridized with all 2080 pluralities of a detectable oligonucleotide probe of 6 bp, probe maps derived from separate cells, etc.). Such software may also be used to assemble restriction maps to generate genome wide restriction maps based on overlaps from restriction fragments derived from separate cells. Further, the software can facilitate assembly of at least one genome wide probe map with at least one genome wide restriction map to generate a genome wide hapolotype sequence and/or a correction of errors in the original probe maps and/or restriction maps.

An exemplary minimum redundancy of about 50× may be used to generate genome wide probe maps and/or genome wide haplotype sequences and recover from most errors (except, e.g., a residual sizing error) with high confidence. Such exemplary error recovery is described, e.g., in T. Anantharaman et al. "A Probabilistic Analysis of False Positives in Optical Map Alignment and Validation," WABI2001, August 2001; and in T. Anantharaman et al. "Genomics via Optical Mapping III: Contiging Genomic DNA and variations," ISMB99, August 1999. Conventional Optical Mapping technology may be used for construction of genome wide restriction maps of various microbes as described, e.g., in J. Lin et al. "Whole-Genome Shotgun Optical Mapping of *Deinococcus radiodurans*." Science, 285:1558-1562, September 1999; in Z. Lai. et al., "A Shotgun Sequence-Ready Optical Map of the Whole *Plasmodium falciparum* Genome," Nature Genetics, 23(3): 309-313, 1999; in A Lim et al., "Shotgun optical maps of the whole *Escherichia* cob O157:H7 genome," Genome Research, 11(9): 1584-93, September 2001; and in S. Zhou et al., "A Whole-Genome Shotgun Optical Map of *Yersinia pestis* Strain KIM." Appl. Environ. Microbiol., 68(12): 6321-6331, 2002.

The exemplary procedures can be used to generate genome wide haplotype maps (e.g., for each chromosome). Additionally, the exemplary procedures described herein may also be used to generate genome wide non-haplotype maps, e.g., genotype maps. These maps may be generated from optical mapping data (e.g., optical mapping probe data and/or optical mapping restriction data) based on Bayesian/Maximum-Likelihood estimation as described, e.g., in T. Anantharaman et al. "A Probabilistic Analysis of False Positives in Optical Map Alignment and Validation," WABI2001, August 2001; and in T. Anantharaman et al. "Genomics via Optical Mapping III: Contiging Genomic DNA and variations," ISMB99, August 1999. More recent exemplary procedures for generating haplotype maps from optical mapping data may extend the older procedures to handle a mixture hypothesis of pairs of maps for each chromosome, corresponding to the correct ordered restriction maps of the two parental chromosomes. Such an exemplary procedure is described, e.g., in T. Anantharaman et al. "Fast and Cheap Genome wide Haplotype Construction via Optical Mapping," Proceedings of PSB, 2005.

Statistical modeling of the errors may be straightforward. However, a combinatorial version of the problem for finding a best map assembly is theoretically computationally infeasible, i.e., it may be NP-hard and there may be no corresponding polynomial-time approximation scheme (PTAS). This theoretical high complexity applies to both non-haplotype and haplotype map assembly cases as well as to other related variants as described, e.g., in T. Anantharaman et al. "Genomics via Optical Mapping II: Ordered Restriction Maps," Journal of Computational Biology, 4(2): 91-118, 1997; and in B. Mishra and L. Parida, "Partitioning Single-Molecule Maps into Multiple Populations: Algorithms And Probabilistic Analysis," Discrete Applied Mathematics, 104(1-3): 203-227, August, 2000.

Such combinatorial results may suggest that any procedure used to find the best map assembly may utilize computational time that is super-polynomial (e.g., exponential) with respect to the size of the input data (under a widely-accepted hypothesis that P # NP). However, by appropriate design of an experimental set-up, it may be possible to only address easy instances of a normally infeasible problem, as described, e.g., in T. Anantharaman et al. "A Probabilistic Analysis of False Positives in Optical Map Alignment and Validation," WABI2001, August 2001.

For example, it may be possible to partition the sets of possible input data into two groups: an "easy" group having sufficiently low error rates or sufficiently high data coverage to compensate for the error rates, where probabilistic polynomial time solutions to the problem are possible, and a "hard" group for which no polynomial time solution may be known. Further, it may be relatively easy to classify a data set based on the amount of data and the error rates of the data as described, e.g., in T. Anantharaman et al. "A Probabilistic Analysis of False Positives in Optical Map Alignment and Validation," WABI2001, August 2001. The exemplary transition between the two data types of data sets may be quite sharp, which may result in a "0-1" law for useable data. This insight and its prudent exploitation may be useful in using optical mapping techniques to reliably generate a genome wide haplotype sequence, and it may be useful for scaling sequencing technology to handle complete genomes.

The exemplary genome wide haplotype sequence generated as described herein may exclude short repeats smaller than the 200 bp resolution of the map due to a variant of the "Positional Sequencing by Hybridization" (PSBH) problem, which is described, e.g., in A. Ben-Dor et al., "On the Complexity of Positional Sequencing by Hybridization," J. Comp. Bio, 8(4): 361-371, 2001. Even though the PSBH problem is known to be NP-complete, in practice, it and other such computational obstacles may be overcome using a heuristic procedure that may compute the sequence, or a majority thereof, in linear time, leaving just a few repetitive regions unresolved or with an approximate sequence. Such a scenario may be inferred, e.g., from A. Ben-Dor et al., "On the Complexity of Positional Sequencing by Hybridization," J. Comp. Bio, 8(4): 361-371, 2001. An exemplary embodiment of such a heuristic procedure is described in greater detail herein in Example 2.

A few small regions in the sequence may not be resolved because of for example, the heuristic nature of a particular embodiment of the PSBH procedure, or the presence of a few unusable oligonucleotide probes among the ones selected. However, these gap regions may be filled in by any traditional sequence finishing method, or may even be simply omitted when the pre-defined accuracy and completeness goal is determined to have been met.

Described herein, are exemplary heuristic procedures that may produce a genome wide haplotype sequence, which for a diploid organism, e.g., humans, may be twice the size of a traditional sequence. This exemplary feature of the heuristic procedure described herein may respond to the critical importance of haplotype information in performing comparative genomic studies, and may be largely unaddressable by other sequencing technologies. In addition, genome wide haplotype sequences generated as provided herein may hold more promise in many biomedical applications (e.g., LOH, or loss-of-heterozygosity in cancer).

The exemplary total cost for determining a genome wide haplotype sequence for a human (about 6 Gb) may be dominated by the cost to image standard 20 mm by 20 mm regions on a microscope, e.g., a fluorescent microscope, at a resolution of 1 pixel every 75 nm. An exemplary design for such microscope system, designed to minimize cost and maximize throughput, is described, e.g., in Anantharaman et al., A Proposal to NIH for a Novel Whole Genome Sequencing Technology (Unpublished), 2005, and may be based on conventional components that may image a large number of double stranded nucleic acid molecules, e.g., on coverslips, per day. For example, each slide may be imaged twice, e.g., once to locate weakly detectable oligonucleotide probes, then again to locate distances between restriction sites of a common restriction enzyme, e.g., by using a nucleic acid molecule staining dye (e.g., YOYO-1). In situations where sizing accuracy of genome wide probe maps may be less than what is desirable to meet the preselected accuracy goals, a variant embodiment may use, for example, about 8000 oligonucleotide probes with average probe site intervals of about 8 Kb.

Several exemplary techniques may be used to further increase throughput and to reduce costs associated with this technology, e.g., by up to two orders of magnitude or more. For example, certain exemplary embodiments of the present disclosure may include the use of customized fluorescent microscopes and custom VLSI chips for high throughput CCD imaging. These exemplary technology improvements may result in a reduced total cost.

Figure 2:
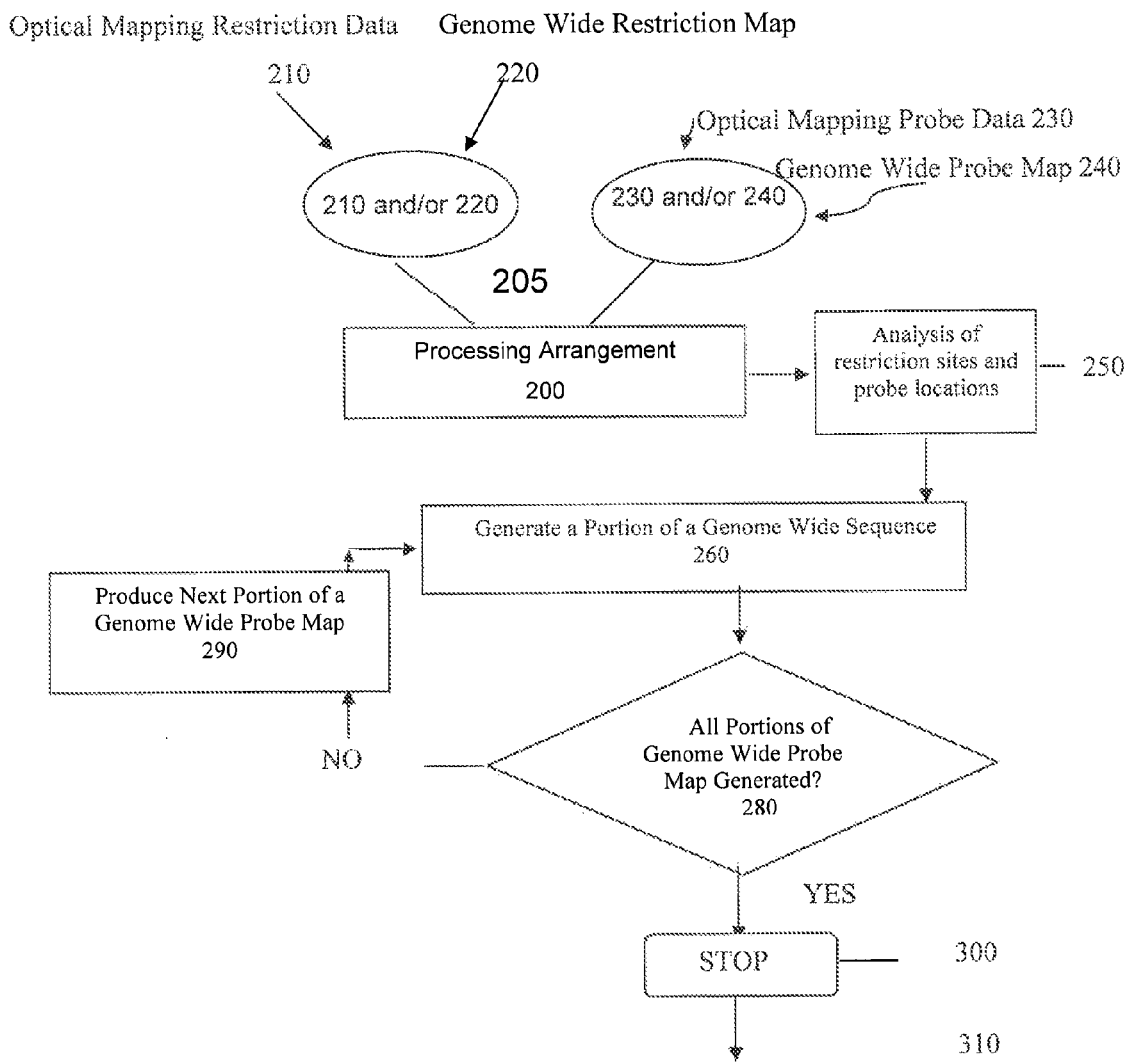
FIG. 2 is a combination of a system and a further flow diagram in accordance with another exemplary embodiment of the present disclosure.

FIG. 2 shows a diagram of a further exemplary embodiment of a combination of a method and a system for generating a genome wide haplotype sequence. The exemplary method may be performed by a processing arrangement 200 such as, but not limited to, a computer with a microprocessor, and can be used with instructions provided on an computer-accessible medium. The processing arrangement receives either or both of:

(a) optical mapping restriction data 210, which may be, for example, used to generate a genome wide restriction map, and/or (b) at least one genome wide restriction map 220, e.g., a database of genome wide restriction maps.

In addition to receiving either or both optical mapping restriction data 210 and at least one genome wide restriction map 220, the processing arrangement can also receive either or both of:

(c) optical mapping probe data 230, which may be for example, from a plurality of detectable oligonucleotide probes hybridized to at least one double stranded nucleic acid molecule cleaved with at least one restriction enzyme, and/or (d) at least one genome wide probe map 240, e.g., a database of genome wide probe maps.

In step 250, the processing arrangement can analyze either or both optical mapping restriction data 210 and/or at least one genome wide restriction map 220 in conjunction with either or both optical mapping probe data 230 and/or at least one genome wide probe map 240. In step 260, the processing arrangement may determine distances between restriction sites of either or both optical restriction data 210 and at least one genome restriction map 220, and can locate detectable oligonucleotide probes of either or both optical mapping probe data 230 and at least one genome wide probe map 240. Such probes are likely associated with at least one chromosome and using which, a portion of at least one genome wide haplotype sequence can be produced. In step 280, the processing arrangement can determine whether all portions of at least one genome wide haplotype sequence is produced. If not, a next portion of the at least one genome wide haplotype sequence may be produced in step 290. If all portions have been produced, the exemplary method stops in step 300, whereby the processing arrangement 200 can use a procedure to combine all the portions to generate a genome wide haplotype sequence.

As shown in FIG. 2, the processing arrangement 200 may be provided with an input arrangement 205, which may include, e.g., a wired network, a wireless network, the Internet, an intranet, etc. In addition, the processing arrangement 200 may be provided with an output arrangement 310 which may include, e.g., a wired network, a wireless network, the Internet, an intranet, etc.

EXAMPLES

A description of certain exemplary embodiments of the present disclosure is provided herein. Included in such description is how conventional optical mapping technology may generate restriction maps of a single double stranded nucleic acid molecule. Such description may be generally applied to the use of optical mapping technology to generate probe maps (see Example 1). Further, a description of a variation of the Gentig/Haptig procedure (Anantharaman et al., "Fast and Cheap Genome wide Haplotype Construction via Optical Mapping," Proceedings of PSB, 2005) that may be used to assemble such restriction maps and/or probe maps into a genome wide probe map and/or haplotype sequence is described in Example 2. Described in Example 3 is a demonstration that robust statistical models of chemical processes may be combined with efficient error-resilient procedures to generate genome wide probe maps and/or genome wide haplotype sequences.

Example 1

Conventional Optical Mapping Technology to Generate Restriction Maps

Uncloned DNA (e.g., DNA directly extracted from cells by lysing) can be randomly sheared into 0.1-2 Mb pieces and attached to a charged glass substrate, where it is reacted with a restriction enzyme, then stained with a fluorescent dye. Such a technique is described, e.g., in J. Jing et al., "Automated High Resolution Optical Mapping Using Arrayed, Fluid Fixated, DNA Molecules," Proc. Natl. Acad. Sci. USA, 95:8046-8051, 1998. The restriction enzyme cleavage sites appear as breakages in the DNA under fluorescent microscope.

Tiled images of the surface may be collected automatically using a fluorescent microscope with a computer controlled x-y-z sample translation stage. The images can be analyzed by computer procedures to detect bright DNA molecules and locate breakages, which correspond to restriction enzyme cleavage sites. The approximate size of the distances between restriction sites is estimated based on the integrated fluorescent intensity relative to that of a standard DNA fragment (e.g., small cloned piece of DNA, for example, some Lambda Phage Clones) that has been added to the sample. In other words, a known length and restriction map of the standard DNA fragment is used to recognize the distances between restriction sites in the DNA.

Recognition of standard DNA molecules can be improved using a fluorescent probe that hybridizes only with the ends of the standard DNA, which renders standard DNA molecules more readily recognizable in the probe image to help ensure that complete (e.g., unbroken) standard DNA molecules are present.

Example 2

Exemplary Procedures to Generate Genome Wide Probe Maps and/or Haplotype Sequences Exemplary techniques can be used to combine multiple probe maps and/or portions of genome wide probe maps (e.g, indicating the location of small 6 bp LNA probes) to generate a genome wide probe map and/or genome wide haplotype sequence. For example, probe maps can be aligned with each other, thus effectively producing one genome wide probe map that may show most or all locations where the oligonucleotide probes hybridized.

Such exemplary probe maps can be created on a scaffold of restriction maps by using a restriction enzyme sites located and determined is present in all maps (e.g., all probe maps and all restriction maps). Each probe map may be independently aligned with at least one genome wide restriction map created using the same restriction enzyme. Corresponding locations in other haplotype may be checked for any match, since the two haplotypes for most mammalian genomes may be very similar, and the procedure may use such a test to ensure that the map is aligned with the correct haplotype.

The alignments of all the probe maps against at least one genome wide restriction map can be saved and used to define a consensus map based on all the locations of all the probes and the distances between the restriction sites of the genome wide restriction map. The exact interleaving order of the different probe sites may be undetermined for nearby probes since the location in each map may be known only to within about 200-400 bp. Furthermore, because the data may be separated by chromosome (and haplotype), a parallel technique can optionally be used for further analysis which can be applied separately to each chromosome (and haplotype). Additionally, because the data from all probes may be naturally separated by common restriction sites, another parallel technique can optionally be used to further analyze each restriction fragment (and haplotype) separately.

For example, even with a small incomplete set of probes, although exact genome wide haplotype sequences may not be determinable, a hybrid probe/restriction map may be used for many purposes such as, e.g., verifying a shotgun sequence assembly, haplotype phasing, locating point-mutations, translocations and copy-number fluctuations for oncogenomic applications, etc.

Genome wide haplotype sequences can be inferred or derived from the aligned probe maps. For example, it is possible to use 6 bp probes, but other probe sizes may also be used or probes with interspersed universal bases may be substituted.

Since exemplary approximate locations (within about 200-400 bp) of each 6 bp L-mer in the chromosome sequence may be known, there is sufficient sequence information in the data, e.g., an equivalent of 6 bp sequence reads to cover the chromosome 6× times at any location (assuming all 6-bp probe maps are complete). However, a shotgun sequence assembler may not be capable of assembling a genome from such data because the "sequence reads" of 6 bp may be too short to yield reliable overlap information. However, there may be valuable additional information present relating to the location of each 6 bp "sequence read" to within about 400 bp in the genome.

For example, if a probe site corresponding to ACGTCG at some location can be considered, it may be sufficient to look at regions within about 200 bp in each of the 4 probe maps corresponding to probes CGTCGA, CGTCGC, CGTCGG, CGTCGT. The correct extension of the sequence ACGTCG on the right may correspond to one of these 4 probes, which may preferably be located at the same location (to within the location measurement error of about ±200 bp). In this way, the exemplary technique described herein can be capable of repeatedly extending the sequence to the right. However, one or more of the other 3 probes may also include a site (or a reverse complement of the site) nearby, e.g., within about 200 bp, and therefore imply another candidate for the next base pair. In such situation, the exemplary technique may be used to consider this additional extension, until the sequence assembly cannot be extended further.

It may not be readily apparent whether the number of extensions to be carried along could expand exponentially (or not), based on the uncertainty in the probe site locations of about ±200 bp. However, certain heuristics, including one described in detail herein below, can ensure that the number of extensions will only rarely increase exponentially. In such cases, certain predetermined maximum number of best scoring extensions can be retained. Simulation results, described below, indicate that such cases are rare (e.g., covering about 2% of the human genome) and even in those rare cases, the exemplary techniques described herein can assemble an approximate sequence with 99% accuracy. For most of the human genome which do not generate an exponential number of extensions, the exemplary techniques described herein can produce a sequence with an accuracy better than 99.99%. This exemplary technique represents an important innovation in the field of sequence assembly.

The computational issue described above can be considered a special case of a well-studied problem in Computational Biology called the "Positional Sequencing by Hybridization" (PSBH) problem. The PSBH problem can be derived from an older problem called the "Sequencing by Hybridization" (SBH) problem. In its classical form, SBH was created to be used with densely packed gene-chips, but the theoretical size of such gene-chips which may be needed to sequence large genomes can be impractically large. Thus, the SBH approach has not yet been used to generate practical (cost-effective) sequencing devices. While the PSBH problem may suggest a possible way to avoid the need for such large amounts of data, there has been no effective technology capable of generating such data. Additionally, the PSBH problem, in almost all cases, is generally NP-complete which results in an exponential computation time. The combination of single-molecule technology together with the PSBH procedure that can be computed in linear time, as described herein, can allow both the amount of data that needs to be collected, and the computation time, to become linear with respect to the size of a sequence being assembled. This exemplary technique can thus provide a practical technology based on SBH or PSBH.

The SBH problem may be stated as follows: for a particular sequence, a list of all L-mers in the sequence can be provided (which may include, e.g., the number of times each L-mer occurs in the sequence). An objective is to reconstruct the sequence from this "L-mer spectrum." This problem can be abstracted from an attempt to sequence a short nucleic acid molecule (e.g., about 1 Kb) by first amplifying it (e.g., using PCR or cloning), hybridizing it with an array of all L-mer probes, and recording which probes hybridize with the nucleic acid molecule of unknown sequence. The SBH problem may be solved by building a de Bruijn graph as described, e.g., in P. Pevzner "L-tuple DNA sequencing: Computer Analysis," J. Biomol. Struct. Dyn. 7: 63-73, 1989. Vertices in this de Bruijn graph may correspond to possible (L-1)-mers and a directed edges may be added for each L-mer in the spectrum, extending from a vertex corresponding to the (L-1)-mer prefix to the neighboring (L-1)-mer suffix. The correct sequence may correspond to one of the Eulerian paths in the de Bruijn graph, although there are cases where the correct sequence may not be determinable, e.g., when there are multiple Eulerian paths. For L=8, unique solutions may exist only for sequences that are up to about 200 base pairs long. This limit can be somewhat improved by using more complex probe sets that include universal (e.g., "Don't care") bases as described, e.g., in F. Preparata et al., "Sequencing-By-Hybridization at the Information-Theory-Bound: An Optimal Algorithm," Brown University, Tech. report, 1999; in F. Preparata et al. "On the Power of Universal Bases in Sequencing by Hybridization," Proceedings of CIBM 3: 295-301, 1999; and in E. Halperin et al., "Handling Long Targets and Errors in Sequencing by Hybridization," J. Comp. Bio., 10(3-4): 483-497, 2003. Although the SBH problem may have an efficient solution, it may not be appropriate for reconstructing large sequences correctly using realistic size arrays.

The PSBH problem is described, e.g., in A. Ben-Dor et al., "On the Complexity of Positional Sequencing by Hybridization," J. Comp. Bio, 8(4): 361-371, 2001. The PSBH problem can assist the computational problem by assuming the following additional information in addition to that provided in the SBH problem: for each L-mer probe, in addition to knowing whether it hybridizes with the unknown sequence (with or without count), constraints can be imposed on the location of the L-mer in the sequence. Such a constraint can have a form of a set of permissible locations for each L-mer (which need not be contiguous). This additional information was assumed in an attempt to allow larger sequences to be assembled. However, the PSBH problem may have a polynomial time solution only if the constraint limits each L-mer to no more than two exact locations on the sequence: If 3 or more locations are possible, then again the reconstruction problem becomes NP-complete. This result is described, e.g., in A. Ben-Dor et al., "On the Complexity of Positional Sequencing by Hybridization," J. Comp. Bio, 8(4): 361-371, 2001. However, if the location constraints have a form of "k" contiguous locations, then the reconstruction problem may be exponential only in "k" rather than in the sequence length m. Theoretically, there may be no efficient procedure that can make use of location information except for the unlikely situation corresponding to P=NP.

In a given data set of probe maps for all 6-mers, there can be multiple instances of each L-mer, for L=6 (about one every 4 Kb on each strand of the DNA) in the sequence. For each instance the location can be constrained to within about 200 base pairs depending on the optical resolution. This situation can correspond to a special case of the PSBH problem, which could be referred to as the "Multiple Positional Sequence by Hybridization" (Multiple PSBH) problem, where there may be separate constraints for each of the multiple instances of each L-mer, resulting in a problem that can be procedurally solved using techniques described herein. By focusing on a small window of about 2000 bp, in which most L-mers may occur only once, it can become practical to solve the standard PSBH problem where separate constraints for multiple instances of each L-mer may not be important. Thus the reconstruction problem may be no larger than exponential in "k", i.e., the range of contiguous locations to which each L-mer can be constrained. In the situation of interest, k=400, such a sequence reconstruction approach based on standard PSBH that is exponential time in "k" may not be useful.

However if each local PSBH problem for each 2000 bp window is solved separately, such an exponential time reconstruction is unlikely to apply to most windows. Thus, a basic procedure as described herein can simply limit the amount of time spent in each window to some upper bound, which may be linear in the window size, in order to reconstruct the sequence in most windows in linear time. This concept forms the basis of the following linear time heuristic. It can be demonstrated that if K, the location uncertainty, is small enough, the sequence in most regions is likely to reconstruct in linear time by using a probabilistic argument. An upper bound of the solution procedure, in the absence of any local time constraint, would still remain exponential in K.

The following exemplary global assumptions can be useful in applying the heuristic procedures described herein: (1) a probe location error is no more than about 10% of the average inter-probe distances, so that for probes with an average distance of 2 Kb: the probe location error may not exceed about ±200 bp; and (2) there are no false negatives or false positives in the probe map, with the probe site location uncertainty being the only error in the maps. This latter assumption may be relaxed as described below. The location uncertainty can be described in terms of a local uncertainty of ±K relative to the nearest restriction site (e.g., about ±200 bp).

A sequence assembly procedure in accordance with exemplary embodiments of the present disclosure can traverse a "virtual" tree of possible sequences (from the left end of each restriction fragment based on the restriction map orientation) in a breadth-first manner, continuously pruning all branches that may be inconsistent with the data. At the root of the tree first level branches are allowed for every 6 bp sequence, whose probe site (or its reverse complement) is observed within 200 bp (e.g., the assumed location uncertainty) of the left end. At all other subsequent nodes of the tree, e.g., only the 4 possible single base pair extensions of the sequence from the root to the current node are considered and those branches for which the corresponding probe site (or its reverse complement) is observed within K by from the "current location" are added. The "current location" can be a length of the sequence from the root to the current node.

In further exemplary embodiments of the present disclosure, other heuristics may be employed, such as, e.g., creating solutions over small windows and combining them in a divide-and-conquer fashion (e.g., "partition-ligation" schemes). For example, an MCMC approach can also be used, where portions of sequences may be randomly reconstructed while keeping other parts frozen. Such approaches may result in greater accuracy at the expense of longer computation times.

In the exemplary "virtual-tree" procedure described herein, most paths down the tree other than the main path can correspond to a correct sequence end shortly after diverging from the main path. For random sequences, exemplary expected branching factors of nodes not on the main path of the tree can be determined as follows:

Extensions to such nodes can be caused by any of the 4 possible sequence extension probes being (possibly randomly) located within K by of a current location. A probe site that occurs every R base pairs (R can average 4096 for 6-mer probes) can be located at random every R/2 base pairs, including reverse complement sites, since the original two corresponding DNA strands may be located next to each other on a surface. Thus, the chance of randomly finding such a particular probe within ±K bp of the current location is 4K/R. The expected number of extensions for all 4 possible probes may therefore be 16K/R, which corresponds to the expected branching factor.

If the number of tree branches generated is to remain bounded for random sequences, the expected branching factor (16K/R) should be less than about 1.0. Along the main path, each node may have 1 correct extension plus 12K/R random extensions. Thus, for random sequences and for any level sufficiently deep in the tree, the expected number of surviving branches can be expressed as $1+12(K/R)/(1-16K/R)$. For example, if K=200 and R=4096, then (16K/R)=0.781 and the expected number of branches will be about 3.68. However if K is increased to 250, then the parameter (16K/R) can increase to 0.9765 and the expected number of branches increases to 32.24. If K>255, the number of tree branches generated becomes unbounded. Thus, there can be a very sharp increase in the number of branches (from a reasonable average of 3.68 branches) that may be tracked in a breadth first search when K is greater than about 200. To handle false negatives in the data, the above exemplary heuristic procedure may be modified to add all possible extensions not supported by data at any point and carry forward these extensions for a limited number of bases. In most cases where no actual false negatives is present the heuristic score of these extensions may drop rapidly and can be discarded. In the rare cases where a false negative is present, the heuristic score of these extensions may be good and may allow these extensions to be continued as normal. Extra probe locations are left after assembling the sequence to correct for false positives. To ensure that the sequence assembly is not terminated too soon, a Bayesian score to estimate the expected amount of false positives in the data is used and termination of the assembly is not considered until the left over probe locations are of reasonable size.

Because the actual human genome sequence is not a random sequence, the preceding description may not be applicable to human genome sequences for several reasons. For example, if there are repeats in a tree, alternate paths can correspond to skipping or adding one or more repeats but may subsequently look identical to the main path. With each new set of sequence repeats, the number of such paths can multiply and hence grow exponentially, which can be avoided by using the exemplary techniques described below.

Each probe site in the map can be labeled with its multiplicity, which is an estimate of the number of overlapping probes near that location that may be based on the fluorescent intensity. Any extension of a path in the graph can be penalized for a probe site that has already been used as many times as its multiplicity in the path so far. Similarly, any final sequence that does not contain enough repeats to explain the observed fluorescent intensity can be penalized. Computing such a penalty requires looking back in the path to count how many times the same probe has been used. Even though the path need only be considered as far back as the previous restriction site, this occurrence could be 16000 bases away, so simply scanning back every time a sequence is extended by 1 bp may be very slow. Thus, two extra data structures can be provided and maintained to allow previous probe locations to be located quickly. The first such data structure can be a table of probe locations at select nodes in the tree. At such select nodes, the table can provide the previous location of each of the possible sequences for a probe of a certain length, e.g., 2080 probes for 6-bp probes, along the path back from that node. Only every 64th node along any path will have such a table, which limits the maximum amount of memory required per node to about 130 bytes (2080×4/64).

Typically, the amount of memory used may be much less than this number because the 64th ancestor of many leaf nodes is actually the same node, so the number of nodes that have a table can be much smaller than otherwise expected. To find the first instance of any particular base in the look-back path, the path can be scanned back up to 64 nodes to find one of these special nodes. To find the remaining probe locations in the path, a single pointer can be added at each node that refers to the previous node having the same probe as the current node (or, alternatively, a special pointer NIL can be added if no such previous node exists). Thus, the computational effort to find all previous instances of a specific probe starting at any node can be no more than 64 steps, plus the number of previous probe locations.

At each level of the tree, all paths having the same last 5 bases may be combined, provided they all have the same or similar last location for each probe, so that the alignment error from the next probe location will be the same. Only the "best" path (e.g., the one with the smallest total probe location errors) would be extended, and the other paths can be merged at the point of similarity (or alternate paths can be discarded if tracking ambiguous solutions is not desired).

The sequence assembly heuristic described above can be achieved in linear time because it is possible to limit the number of paths at any depth of the tree to some maximum number (which can be referred to as the "beam width"). Whenever the number of paths exceeds this maximum number, a sufficient number of worst scoring paths can be discarded such that the remaining number of paths drops below the beam width. There can be a small risk that the correct path (which may not be a best scoring path) may be discarded too hastily. Simulations indicate that for random sequences, such an early discarding of the correct path may not occur if the beam width is set to the equivalent of 2 Gigabytes of memory. For a human genome sequence, the correct sequence may be discarded about once every 50 kb. Even in such cases, the incorrect sequence assembled may be usually incorrect only in a few bases (typically 10-30 bp) around the region where the beam width was exceeded. Such errors can be reduced further, e.g., by adding an "annealing" step in which regions of the assembled sequence that are likely to contain errors (e.g., regions where the beam width was exceeded) may be subsequently reassembled locally while relying on the higher level of correctness of the sequence on either side of the problem region.

Example 3

Combination of Statistical Models of Chemical Processes with Resilient Procedures Table 1 and Table 2 below show exemplary results of running the heuristic sequence assembly procedure on simulated data derived from random sequences (Table 1) and human chromosome 1 (Table 2). Both tables show the sequence error rate per 10,000 bases. Thus an error rate of 1 would correspond to an accuracy of 99.99%. Tables 1 and 2 show the error rate for difference size probes, some of which include universal bases. The location of universal and regular bases is shows as a pattern using the character x for each regular base and a dash (-) for each universal base. To generate the simulated data, a random DNA sequence was used and computed the probe map of a single restriction fragment of size 1 kb, for all possible probes for the probe type chosen was computed. For example, for a probe with 6 specific bases and 4 universal bases and the pattern xx-x--x-xx for the specific bases, there are a total of 2080 distinct possible sequences for a probe of a certain length, excluding reverse complements. For each probe map data error was simulated under the following assumptions for single DNA molecules: Probe location Standard Deviation=240 bases; Data coverage per probe map=50×; Probe hybridization rate=30% (which means false negative rate is 70%), and false positive rate of 10 probes per megabase, uniformly distributed.

Instead of simulating each single DNA molecule, the average error rate was analytically estimated in the probe consensus map based on the above assumptions: Probe location Standard Deviation=60 bases; False Positive rate <2.4%; False Negative rate <2.0%. Using these estimated error rates for probe consensus maps, errors were randomly introduced at the above rates into each of the 2080 simulated probe maps for each of the 2080 distinct possible sequences for a probe of 6 bp, (see, above). The exemplary heuristic sequence assembly procedure was then executed, and then aligned using an exemplary Smith-Waterman alignment against the presumed correct sequence produced originally. The total number of single base errors (mismatches+deletions+insertions) was counted. This experiment was then repeated until a total of 200,000 bases of sequence had been simulated to produce statistics for the average error rate per 10,000 bases. For Table 2, the experiment was repeated starting with 200 blocks of 1000 bases drawn from the actual sequence of human chromosome 1 (Build 35). In Table 2, it was also possible to show the error rate not counting errors in the number of short repeats (the column labeled "Errors Without Repeats"). Table 2 also shows the number of bases that could not be reliably assembled (per 10,000 bases), when the heuristic procedure ran out of memory and was forced to discard possible solution states and the corresponding nearby 10 bases were marked as "not known". If these bases were determined based on the remaining possible states, their error rates may be as high as 10%. No significant number of such instances were encountered for random sequences, hence this column is not shown in Table 1.

TABLE 1

Error rates for random sequences

| Probe Pattern | Universal Bases | Total Error Rate |
|---|---|---|
| xxxxx | 0 | 1673.8 |
| xxxxxx | 0 | 255.1 |
| xxxxxxx | 0 | 39.6 |
| xxxxxxxx | 0 | 3.7 |
| xxxxxxxxx | 0 | 0.2 |
| xxx-xxx | 1 | 35.9 |
| xx-xx-xx | 2 | 4.4 |
| xx-x-x-xx | 3 | 2.7 |
| xx-x--x-xx | 4 | 0.1 |

TABLE 2

Exemplary Error rates for human chromosome 1

| Probe Pattern | Universal Bases | Total Error Rate/10000 | Errors without Repeats/10000 | No Call Rate per 10000 |
|---|---|---|---|---|
| xx-x--x-xx | 4 | 18.5 | 1.70 | 75 |
| xx-x----x-xx | 6 | 14.1 | 1.10 | 21 |
| xx-x-------x-xx | 9 | 10.4 | 0.75 | 25 |

TABLE 3

Exemplary Percentage of correct assembly of a sequence for different probe patterns

| Probe Pattern | Percentage Correct |
|---|---|
| x-x-x-----x-x-x | 91.69 |
| x-x---x-x---x-x | 91.92 |
| x---x-x-x-x---x | 92.24 |
| x---xx---xx---x | 97.88 |
| x--x-x-x-x--x | 98.47 |

TABLE 3-continued

Exemplary Percentage of correct assembly of a sequence for different probe patterns

| Probe Pattern | Percentage Correct |
|---|---|
| x--x-x---x-x--x | 98.75 |
| x--xx-----xx--x | 98.77 |
| x----xx-xx----x | 98.88 |
| xx---x--x---xx | 98.99 |
| xxx--------xxx | 99.12 |
| xx-x-------x-xx | 99.13 |
| xx--x-----x--xx | 99.21 |
| x-xx-------xx-x | 99.23 |
| xx----x-x----xx | 99.29 |
| x-x--x---x--x-x | 99.58 |

TABLE 4

Coverage of position i by ungapped probes of size 4

|   |   |   | i |   |   |   |
|---|---|---|---|---|---|---|
| x | x | x | x |   |   |   |
|   | x | x | x | x |   |   |
|   |   | x | x | x | x |   |
|   |   |   | x | x | x | x |

TABLE 5

Exemplary Coverage of position i by two different gapped probes of size 4 with two universal bases

|   |   |   | i |   |   |   |   |   |   |   | i |   |   |
|---|---|---|---|---|---|---|---|---|---|---|---|---|---|
| x | x | — | — | x | x |   |   | x | — | x | x | — | x |
|   | x | x | — | — | x | x |   |   | x | — | x | x | — | x |
|   |   | x | x | — | — | x | x |   |   | x | — | x | x | — | x |
|   |   |   | x | x | — | — | x | x |   |   | x | — | x | x | — | x |
|   |   |   |   | x | x | — | — | x | x |   |   | x | — | x | x | — | x |
|   |   |   |   |   | x | x | — | — | x | x |   |   | x | — | x | x | — | x |

As shown in Table 3, even though most of the gapped probes provide good results, some of those probes can be more effective than others. Even if the procedure is sufficiently robust for several choices, a selection of the optimal pattern for a probe can lead to easier reconstruction of a sequence and therefore faster and more accurate results. Exemplary embodiments may be able to predict a priori which patterns are better.

In certain exemplary embodiments that use ungapped probes, as illustrated in Table 4, a specific position i of the sequence can be covered by k different probes (e.g., when the size of the probe is k) and the coverage of the surrounding 2 k-2 can then be maximal. There can be gapped probes that are deficient in this maximum coverage. However, as provided in Table 5, each position can still be covered by k probes, and the size of the probe can include both solid and universal bases. Depending on the probe pattern, the coverage can be different. This difference of coverage can determine how "good" and "bad" patterns differ. For example, some probe patterns may facilitate a better mixing of solid and universal bases. Exemplary embodiments can represent the different coverages of the probes by their graph and adjacency matrices. For example, the matrix for the right pattern of Table 6 can include the following where the (i, j) entry shows the number of positions at which the bases aligned to i agree with the base aligned j:

TABLE 6

Exemplary Alignment Distance Matrix $$\begin{bmatrix} 6 & 1 & 2 & 2 & 0 & 1 \\ 1 & 6 & 1 & 2 & 2 & 0 \\ 2 & 1 & 6 & 1 & 2 & 2 \\ 2 & 2 & 1 & 6 & 1 & 2 \\ 0 & 2 & 2 & 1 & 6 & 1 \\ 1 & 0 & 2 & 2 & 1 & 6 \end{bmatrix}$$

One exemplary "good" indicator of how well exemplary probes mix the local information can include the value of the spectral gap of those matrices. The spectral gap can include the difference between the first and the second eigenvalues of a matrix. If the spectral gap is large, it can be easier for information to travel in an exemplary graph between any two points while a small spectral gap can mean that it is hard for information to diffuse in the graph. Thus, in certain exemplary embodiments, if an exemplary probe pattern has a big spectral gap, despite the probe being gapped, the coverage of the few bases around any particular base of interest can be reasonably good to provide some auxiliary information to confirm an alignment.

Exemplary matrices can be normalized so that they are stochastic and the first eigenvalue can be 1 for each of them. Exemplary embodiments can then compute the second eigenvalue of the matrices. This can lead to at least two exemplary effects. First, the exemplary probes that were not "good" to assemble the sequence can get a second eigenvalue of 1 (or very close to 1), leading to a null (or very small) spectral gap. By simply examining the eigenvalues, exemplary embodiments can predict the clusters of "good" and "bad" probes.

The foregoing merely illustrates the principles of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the present disclosure and are thus within the spirit and scope of the present disclosure. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A non-transitory computer-accessible medium having stored thereon computer executable instructions for generating a genome wide probe map which, when the executable instructions are executed by a processing arrangement, configure the processing arrangement to perform a procedure comprising:

(a) obtaining at least one plurality of at least one detectable oligonucleotide probe hybridized to at least one double stranded nucleic acid molecule cleaved with at least one restriction enzyme; and (b) detecting the location of the plurality of at least one detectable oligonucleotide probe to generate a genome wide probe map.

2. The computer-accessible medium of claim 1, wherein the at least one detectable oligonucleotide probe is of the type of at least one of a Locked Nucleic Acid oligonucleotide probe, a Peptide Nucleic Acid oligonucleotide probe, a Triplex Forming Oligonucleotide probe, an Ethylene Nucleic Acid oligonucleotide probe, a polyamine oligonucleotide probe, or an oligonucleotide probe comprising any mixture of the above.

3. The computer-accessible medium of claim 2, wherein at least one detectable oligonucleotide probe has a length of at least one of 6 base pairs, 7 base pairs, 8 base pairs, 9 base pairs, 10 base pairs, 11 base pairs, 12 base pairs, 13 base pairs, 14 base pairs, and 15 base pairs.

4. The computer-accessible medium of claim 3, wherein the at least one detectable oligonucleotide probe includes at least one of solid nucleotide (adenine "A", thymine "T", cytosine "C", guanine "G") and at least one gap nucleotide, wherein a pattern including the at least one solid nucleotide and the at least one gap nucleotide is known.

5. The computer-accessible medium of claim 4, wherein the at least one detectable oligonucleotide probe is selected according to a quality metric that is based at least in part on the selected pattern of the solid and gap nucleotides.

6. The computer-accessible medium of claim 5, wherein the quality metric for the selection is at least 0.1.

7. The computer-accessible medium of claim 5, wherein the quality metric of the at least one detectable oligonucleotide probe is based at least in part on a spectral-gap metric based at least in part on a matrix derived from the pattern of the solid and gap nucleotides.

8. The computer-accessible medium of claim 1, wherein the at least one detectable oligonucleotide probe is labeled with a fluorescent label.

9. The computer-accessible medium of claim 8, wherein the processing arrangement is further configured to, between the obtaining and detecting techniques, obtain at least one further plurality of at least one further detectable oligonucleotide probe hybridized to the at least one double stranded nucleic acid molecule cleaved with the at least one restriction enzyme.

10. The computer-accessible medium of claim 9, wherein the at least one further detectable oligonucleotide probe is of the same type as the at least one detectable oligonucleotide probe.

11. The computer-accessible medium of claim 10, wherein the at least one further detectable oligonucleotide probe is of the same length as the at least one detectable oligonucleotide probe.

12. The computer-accessible medium of claim 11, wherein the at least one further detectable oligonucleotide probe is labeled with a further fluorescent label.

13. The computer-accessible medium of claim 12, wherein the processing arrangement is configured to, during the detection, generate a first probe map for the at least one oligonucleotide probe hybridized to the at least one double stranded nucleic acid molecule cleaved with the at least one restriction enzyme and a second probe map for the at least one further oligonucleotide probe hybridized to at least one double stranded nucleic acid molecule cleaved with the at least one restriction enzyme.

14. The computer-accessible medium of claim 13, wherein the processing arrangement is configured to, during the detection, generate a genome wide probe map by aligning the restriction sites of the first probe map and the second probe map.

15. The computer-accessible medium of claim 8, wherein the processing arrangement is further configured to, between the obtaining and detecting techniques, hybridize the at least one double stranded nucleic acid molecule cleaved with the at least one restriction enzyme with a plurality of at least one different detectable oligonucleotide probe, wherein each of the at least one different detectable oligonucleotide probe has one of all possible sequences for a reference detectable oligonucleotide probe sized as the at least one detectable probe.

16. The computer-accessible medium of claim 15, wherein the processing arrangement is configured to, during the detection, generate a probe map for each performed hybridization.

17. The computer-accessible medium of claim 16, wherein the processing arrangement is configured to, during the detection, generate a genome wide probe map by aligning the restriction sites of each probe map.

18. The computer-accessible medium of claim 1, wherein the double stranded nucleic acid molecule is deposited on a coverslip.

19. The computer-accessible medium of claim 1, wherein the double stranded nucleic acid molecule is elongated and fixed using a large fluid flow.

20. The computer-accessible medium of claim 1, wherein the double stranded nucleic acid molecule is deposited on a surface overlayed with microchannels through which the molecules flow at a suitable velocity for depositing the molecules in a well stretched manner.

21. The computer-accessible medium of claim 1, wherein the processing arrangement is configured to perform the detection technique with a microscope of at least one of an optical microscope, a Total Reflection Fluorescent Microscope, and an atomic force microscope.

22. The computer-accessible medium of claim 1, wherein the double stranded nucleic acid is stained with a DNA dye.

23. The computer accessible medium of claim 22, wherein the dye is at least one of YOYO-1, POPO, and JOJO.

24. The computer accessible medium of claim 1, wherein the processing arrangement is configured to, during the detection, generate the genome wide probe map using a heuristic alignment procedure.

25. The computer accessible medium of claim 1, wherein the processing arrangement is configured to, during the detection, generate the genome wide probe map using a Bayesian procedure with a prior statistical model of restriction activities and probe hybridization activities.

26. A method for generating a genome wide probe map comprising:
  (a) obtaining a plurality of detectable oligonucleotide probes hybridized to at least one double stranded nucleic acid molecule cleaved with at least one restriction enzyme, wherein at least one of the detectable oligonucleotide probes includes at least one solid nucleotide and at least one gap nucleotide, and wherein a nucleotide pattern including the at least one solid nucleotide and the at least one gap nucleotide is known; and
  (b) detecting the location of the detectable oligonucleotide probes to generate a genome wide probe map.

27. A system for generating a genome wide probe map comprising:
  a computer hardware arrangement configured to:
  (a) obtain a plurality of detectable oligonucleotide probes hybridized to at least one double stranded nucleic acid molecule cleaved with at least one restriction enzyme, wherein at least one of the detectable oligonucleotide probes includes at least one solid nucleotide and at least one gap nucleotide, and wherein a nucleotide pattern including the at least one solid nucleotide and the at least one gap nucleotide is known; and
  (b) detect the location of the detectable oligonucleotide probes to generate a genome wide probe map.

* * * * *